(12) United States Patent
Kirk et al.

(10) Patent No.: US 8,284,394 B2
(45) Date of Patent: Oct. 9, 2012

(54) METHODS AND SYSTEMS FOR DETERMINING A CHARACTERISTIC OF A WAFER

(75) Inventors: Michael D. Kirk, San Jose, CA (US); Christopher F. Bevis, Los Gatos, CA (US); David Adler, San Jose, CA (US); Kris Bhaskar, San Jose, CA (US)

(73) Assignee: KLA-Tencor Technologies Corp., Milpitas, CA (US)

( * ) Notice: Subject to any disclaimer, the term of this patent is extended or adjusted under 35 U.S.C. 154(b) by 567 days.

(21) Appl. No.: 11/673,150

(22) Filed: Feb. 9, 2007
(Under 37 CFR 1.47)

(65) Prior Publication Data
US 2008/0013083 A1      Jan. 17, 2008

Related U.S. Application Data

(60) Provisional application No. 60/772,418, filed on Feb. 9, 2006.

(51) Int. Cl.
*G01N 21/00*     (2006.01)

(52) U.S. Cl. ............. 356/237.5; 356/237.1; 356/237.2

(58) Field of Classification Search .... 356/237.1–241.6, 356/426–431, 600–640
See application file for complete search history.

(56) References Cited

U.S. PATENT DOCUMENTS

| | | | |
|---|---|---|---|
| 4,162,126 A * | 7/1979 | Nakagawa et al. | 356/237.2 |
| 4,410,278 A * | 10/1983 | Makihira et al. | 356/445 |
| 4,845,558 A | 7/1989 | Tsai et al. | |
| 4,898,471 A | 2/1990 | Vaught et al. | |
| 5,027,122 A * | 6/1991 | Wieler | 342/26 D |
| 5,132,786 A * | 7/1992 | Ishiwata | 358/500 |
| 5,355,212 A * | 10/1994 | Wells et al. | 356/237.4 |
| 5,555,315 A | 9/1996 | Itakura | |
| 5,608,453 A | 3/1997 | Gerber et al. | |
| 5,625,451 A | 4/1997 | Schiff et al. | |
| 5,661,408 A * | 8/1997 | Kamieniecki et al. | 324/750.23 |
| 5,712,701 A | 1/1998 | Clementi et al. | |
| 5,813,333 A * | 9/1998 | Ohno | 101/181 |

(Continued)

FOREIGN PATENT DOCUMENTS

JP          Hei11-237226          8/1999

(Continued)

OTHER PUBLICATIONS

U.S. Appl. No. 11/561,659, filed Nov. 20, 2006, Zafar et al.

(Continued)

*Primary Examiner* — Gregory J Toatley
*Assistant Examiner* — Jarreas C Underwood
(74) *Attorney, Agent, or Firm* — Ann Marie Mewherter (57) ABSTRACT

Methods and systems for determining a characteristic of a wafer are provided. One method includes generating output responsive to light from the wafer using an inspection system. The output includes first output corresponding to defects on the wafer and second output that does not correspond to the defects. The method also includes determining the characteristic of the wafer using the second output. One system includes an inspection subsystem configured to illuminate the wafer and to generate output responsive to light from the wafer. The output includes first output corresponding to defects on the wafer and second output that does not correspond to the defects. The system also includes a processor configured to determine the characteristic of the wafer using the second output.

36 Claims, 4 Drawing Sheets

U.S. PATENT DOCUMENTS

| | | | |
|---|---|---|---|
| 5,903,342 A * | 5/1999 | Yatsugake et al. | 356/237.4 |
| 5,909,276 A | 6/1999 | Kinney et al. | |
| 5,991,699 A | 11/1999 | Kulkarni et al. | |
| 6,025,206 A * | 2/2000 | Chen et al. | 438/16 |
| 6,118,525 A | 9/2000 | Fossey et al. | |
| 6,171,975 B1 * | 1/2001 | Hase et al. | 438/745 |
| 6,201,601 B1 | 3/2001 | Vaez-Iravani et al. | |
| 6,265,719 B1 | 7/2001 | Yamazaki et al. | |
| 6,271,916 B1 | 8/2001 | Marxer et al. | |
| 6,507,025 B1 * | 1/2003 | Verbinski et al. | 250/358.1 |
| 6,538,730 B2 | 3/2003 | Vaez-Iravani et al. | |
| 6,552,337 B1 * | 4/2003 | Cho et al. | 850/33 |
| 6,558,853 B1 * | 5/2003 | Kawamura | 430/5 |
| 6,563,577 B2 | 5/2003 | Oomori et al. | |
| 6,596,553 B1 | 7/2003 | Lin et al. | |
| 6,603,877 B1 | 8/2003 | Bishop | |
| 6,636,031 B1 | 10/2003 | Kenmochi et al. | |
| 6,718,526 B1 | 4/2004 | Eldredge et al. | |
| 6,781,688 B2 * | 8/2004 | Kren et al. | 356/237.4 |
| 6,794,885 B1 | 9/2004 | Yasumoto | |
| 6,858,859 B2 | 2/2005 | Kusunose | |
| 6,893,786 B2 * | 5/2005 | Baggenstoss | 430/30 |
| 6,898,305 B2 | 5/2005 | Hiroi et al. | |
| 6,917,419 B2 | 7/2005 | Fielden et al. | |
| 6,917,433 B2 | 7/2005 | Levy et al. | |
| 6,919,957 B2 * | 7/2005 | Nikoonahad et al. | 356/237.2 |
| 7,006,886 B1 | 2/2006 | Huet et al. | |
| 7,038,773 B2 * | 5/2006 | Kuhlmann et al. | 356/237.4 |
| 7,067,819 B2 | 6/2006 | Janik | |
| 7,207,862 B2 * | 4/2007 | Nabeya et al. | 451/5 |
| 7,286,218 B2 | 10/2007 | Tiemeyer et al. | |
| 7,315,642 B2 * | 1/2008 | Bartov | 382/145 |
| 7,339,661 B2 * | 3/2008 | Korngut et al. | 356/237.2 |
| 7,349,079 B2 | 3/2008 | Zhao et al. | |
| 7,359,052 B2 | 4/2008 | Fielden et al. | |
| 7,369,233 B2 | 5/2008 | Nikoonahad et al. | |
| 7,373,277 B1 | 5/2008 | Wu et al. | |
| 7,417,722 B2 | 8/2008 | Bills et al. | |
| 7,528,944 B2 | 5/2009 | Chen et al. | |
| 7,751,046 B2 * | 7/2010 | Levy et al. | 356/401 |
| 2002/0182760 A1 | 12/2002 | Wack et al. | |
| 2003/0011786 A1 | 1/2003 | Levy et al. | |
| 2003/0107736 A1 | 6/2003 | Fujimoto | |
| 2003/0210393 A1 | 11/2003 | Vaez-Iravani et al. | |
| 2003/0228050 A1 | 12/2003 | Geshel et al. | |
| 2004/0066962 A1 | 4/2004 | Sasa et al. | |
| 2004/0095575 A1 | 5/2004 | Woo et al. | |
| 2004/0252879 A1 | 12/2004 | Tiemeyer et al. | |
| 2005/0051728 A1 * | 3/2005 | Miyauchi | 250/339.06 |
| 2005/0094864 A1 | 5/2005 | Xu et al. | |
| 2005/0179910 A1 | 8/2005 | Bartov | |
| 2005/0186670 A1 | 8/2005 | Oh | |
| 2005/0252752 A1 | 11/2005 | Fielden et al. | |
| 2006/0062445 A1 | 3/2006 | Verma et al. | |
| 2006/0091332 A1 | 5/2006 | Nishiyama et al. | |
| 2006/0181700 A1 | 8/2006 | Andrews et al. | |
| 2006/0192948 A1 | 8/2006 | Judell et al. | |
| 2006/0192949 A1 | 8/2006 | Bills et al. | |
| 2006/0192950 A1 | 8/2006 | Judelle et al. | |
| 2006/0256326 A1 | 11/2006 | Bills et al. | |
| 2006/0290923 A1 | 12/2006 | Nakano et al. | |
| 2007/0024998 A1 | 2/2007 | Bills et al. | |
| 2007/0252977 A1 | 11/2007 | Baran et al. | |
| 2008/0004823 A1 | 1/2008 | Matsushita et al. | |
| 2008/0018887 A1 | 1/2008 | Chen et al. | |
| 2008/0129988 A1 | 6/2008 | Saito et al. | |

FOREIGN PATENT DOCUMENTS

| | | |
|---|---|---|
| JP | 2000-002514 | 1/2000 |
| JP | 2002-257518 | 9/2002 |
| JP | 2004-513509 | 4/2004 |
| JP | 2004-524538 | 8/2004 |
| JP | 2008-096430 | 4/2008 |
| KR | 10-1999-0073971 | 10/1999 |
| KR | 10-2001-0001224 | 1/2001 |
| KR | 10-0738809 | 7/2007 |
| WO | 2005/090650 | 9/2005 |
| WO | WO 2006/066135 | 6/2006 |
| WO | WO 2006/066136 | 6/2006 |
| WO | WO 2006/066137 | 6/2006 |
| WO | WO 2006/066138 | 6/2006 |
| WO | WO 2006/066139 | 6/2006 |
| WO | WO 2006/066205 | 6/2006 |
| WO | WO 2006/066206 | 6/2006 |
| WO | WO 2006/066207 | 6/2006 |
| WO | WO 2006/066255 | 6/2006 |

OTHER PUBLICATIONS

U.S. Appl. No. 11/561,735, filed Nov. 20, 2006, Kulkarni et al.
U.S. Appl. No. 60/868,769, filed Dec. 6, 2006, Fouquet et al.
U.S. Appl. No. 60/870,724, filed Dec. 19, 2006, Kulkarni et al.
U.S. Appl. No. 60/883,617, filed Jan. 5, 2007, Park et al.
U.S. Appl. No. 11/680,152, filed Feb. 28, 2007, Chen et al.
U.S. Appl. No. 11/683,696, filed Mar. 8, 2007, Chen et al.
U.S. Appl. No. 11/830,485, filed Jul. 30, 2007, Kulkarni et al.
U.S. Appl. No. 11/855,573, filed Sep. 14, 2007, Wu et al.
U.S. Appl. No. 11/855,581, filed Sep. 14, 2007, Wu et al.
McMillan, Wayne; "Surfscan SP2: Enabling Cost-Effective Production and the 65nm Node and Beyond," Yield Management Solutions, Summer 2004, pp. 14-23.
Larson, C. Thomas; "Measuring Haze on Deposited Metals with Light-Scattering-Based Inspection Systems," MICRO (Sep. 1996), pp. 31-38.
Stover, John C. Optical Scattering: Measurement and Analysis, SPIE Optical Engineering Press, Bellingham, WA (1995).
Elson et al. "Relationship of the total integrated scattering from multilayer-coated optics to angle of incidence, polarization, correlation length, and roughness cross-correlation properties," J.M. et al. Applied Optics, 22, 3207 (1983).
Scheer, B.W. "Development of a physical haze and microroughness standard," SPIE vol. 2862, pp. 78-95 (1996).
Griffith, J.E. et al.; "Characterization of Scanning Probe Tips for Linewidth Measurement," J. Vac. Sci. Technol. B 9(6), Nov./Dec. 1991, pp. 3586-3589.
Malik, Igor J. et al. "Surface Roughness of Si Wafers: Correlating AFM and Haze Measurements," Semiconductors Silicon/1994: Seventh International Symposium on Silicon Materials Science and Technology, ed. H.R. Huff, W. Bergholz and K. Sumino, The Electrochemical Society, Inc. PV 94-10, Pennington, NJ, 1994, p. 1182.
Marx, Egon et al. "Power spectral densities: A multiple technique study of different Si wafer surfaces," J. Vac. Sci. Technol. B 20(1), Jan./Feb. 2002, pp. 31-41.
International Search Report for PCT/US07/61912 dated Feb. 25, 2008.
Holsteynes et al. "The use of unpatterned wafer inspection for immersion lithography defectivity studies." Apr. 2006.
Nemoto et al. "Impact of Silicon Surface Roughness on Device Performance and Novel Roughness Measurement Method," IEEE/SEMI Advanced Semiconductor Manufacturing Conference, 2007.
Chen et al. "Laser Scattering Correlation with Polysilicon Surface Roughness and Impact on Electrical Performance," ISSM 2006.
International Search Report and Written Opinion for PCT/US07/69465 mailed on Sep. 17, 2008.
International Application No. PCT/US05/45781 filed on Dec. 12, 2005.
U.S. Appl. No. 60/974,030 (Bhaskar et al.) entitled Systems and Methods for Creating Persistent Data for a Wafer and for Using Persistent Data for Inspection-Related Functions filed Sep. 20, 2007.
U.S. Appl. No. 61/074,065 (Chen et al.) entitled Computer-Implemented Methods, Computer-Readable Media, and Systems for Determining One of More Characteristics of a Wafer filed Jun. 19, 2008.
U.S. Appl. No. 12/128,426 (Biellak et al.) entitled Systems and Methods for Determining Two or More Characteristics of a Wafer filed Jul. 24, 2008.
U.S. Appl. No. 12/179,260 (Reich et al.) entitled Computer-Implemented Methods for Inspecting and/or Classifying a Wafer filed Jul. 24, 2008.
International Search Report and Written Opinion for PCT/US08/071587 mailed Dec. 17, 2008.

International Search Report and Written Opinion for PCT/US08/075867 mailed Feb. 17, 2009.
Written Opinion and International Search Report for PCT/US2009/045124, mailed Jan. 7, 2010.
Written Opinion and International Search Report for PCT/US2009/051044, mailed Mar. 3, 2010.

Written Opinion for Singapore Patent Application No. 200805887-7 mailed Jun. 21, 2010.
Notice of the Reasons for Refusal for Japanese Patent Application No. 2008-554517 mailed Oct. 18, 2011.

* cited by examiner

METHODS AND SYSTEMS FOR DETERMINING A CHARACTERISTIC OF A WAFER

PRIORITY CLAIM

This application claims priority to U.S. Provisional Application No. 60/772,418 entitled "Methods and Systems for Determining a Characteristic of a Wafer," filed Feb. 9, 2006, which is incorporated by reference as if fully set forth herein.

BACKGROUND OF THE INVENTION

1. Field of the Invention

This invention generally relates to methods and systems for determining a characteristic of a wafer. Certain embodiments relate to determining a characteristic of a wafer using output generated by an inspection system that does not correspond to defects on the wafer.

2. Description of the Related Art

The following description and examples are not admitted to be prior art by virtue of their inclusion in this section.

Fabricating semiconductor devices such as logic and memory devices typically includes processing a specimen such as a semiconductor wafer using a number of semiconductor fabrication processes to form various features and multiple levels of the semiconductor devices. For example, lithography is a semiconductor fabrication process that typically involves transferring a pattern to a resist arranged on a semiconductor wafer. Additional examples of semiconductor fabrication processes include, but are not limited to, chemical-mechanical polishing, etch, deposition, and ion implantation. Multiple semiconductor devices may be fabricated in an arrangement on a semiconductor wafer and then separated into individual semiconductor devices.

Inspection processes are used at various steps during a semiconductor manufacturing process to detect defects on wafers to promote higher yield in the manufacturing process and thus higher profits. Inspection has always been an important part of fabricating semiconductor devices such as integrated circuits. However, as the dimensions of semiconductor devices decrease, inspection becomes even more important to the successful manufacture of acceptable semiconductor devices because smaller defects can cause the device to fail. For instance, as the dimensions of semiconductor devices decrease, detection of defects of decreasing size has become necessary since even relatively small defects may cause unwanted aberrations in the semiconductor devices.

Metrology processes are also used at various steps during a semiconductor manufacturing process to monitor and control the process. Metrology processes are different than inspection processes in that, unlike inspection processes in which defects are detected on a wafer, metrology processes are used to measure one or more characteristics of the wafer that cannot be determined from currently used inspection tools. For example, metrology processes are used to measure one or more characteristics of a wafer such as a dimension (e.g., line width, thickness, etc.) of features formed on the wafer during a process such that the performance of the process can be determined from the one or more characteristics. In addition, if the one or more characteristics of the wafer are unacceptable (e.g., out of a predetermined range for the characteristic(s)), the measurements of the one or more characteristics of the wafer may be used to alter one or more parameters of the process such that additional wafers manufactured by the process have acceptable characteristic(s).

There are, however, a number of disadvantages to using metrology processes and tools to measure one or more characteristics of a wafer for process monitoring and control applications. For example, most metrology tools are relatively slow, particularly compared to inspection systems. Therefore, metrology processes are often performed at one location or a limited number of locations on the wafer such that metrology results may be acquired in a relatively expedient manner. However, many processes used to manufacture semiconductor devices produce wafers that have characteristic(s) that vary across the surface of the wafers. As such, using metrology measurements performed at one location or a limited number of locations on a wafer may not provide sufficient information about the characteristic(s) of the wafers such that the process can be accurately monitored and controlled. Furthermore, using metrology tools to measure characteristics across the wafer for inline monitoring and control applications is not feasible due to the time in which such measurements can be performed. In particular, metrology measurements performed by currently available metrology tools such as surface roughness, resistivity, film thickness, etc. are not suitable for high sampling of wafers for inline monitoring since the measurements will impact (e.g., increase) cycle time in production.

Accordingly, it would be advantageous to develop methods and systems that can be used for determining a characteristic of a wafer (e.g., across substantially an entire area of a surface of the wafer) and for high sampling of wafers in applications such as inline monitoring and control of semiconductor fabrication processes without increasing the cycle time in production.

SUMMARY OF THE INVENTION

The following description of various embodiments of methods and systems is not to be construed in any way as limiting the subject matter of the appended claims.

One embodiment relates to a method for determining a characteristic of a wafer. The method includes generating output responsive to light from the wafer using an inspection system. The output includes first output corresponding to defects on the wafer and second output that does not correspond to the defects. The method also includes determining the characteristic of the wafer using the second output.

In one embodiment, the light from the wafer includes diffusely scattered light. In another embodiment, generating the output includes illuminating the wafer with light produced by a laser. In an additional embodiment, generating the output includes scanning light across the wafer and generating the output across the wafer. In a further embodiment, generating the output includes generating the output across substantially an entire surface of the wafer. In one such embodiment, determining the characteristic includes determining the characteristic using the second output generated across substantially the entire surface of the wafer.

In one embodiment, determining the characteristic includes determining the characteristic of the wafer using the second output and a predetermined correlation between the second output and the characteristic. In another embodiment, determining the characteristic includes determining a value for the second output across an area on the wafer and determining the characteristic from the wafer. In an additional embodiment, the characteristic is an average characteristic across an area on the wafer. In a further embodiment, determining the characteristic includes determining variation in the second output across the wafer and determining the characteristic from the variation. In some embodiments, determining the characteristic includes generating a two-dimensional map of the second output across substantially an entire surface of the wafer and determining the characteristic from the two-dimensional map.

In an embodiment, determining the characteristic includes determining a value for the second output across different areas of the wafer and determining the characteristic for the different areas using the values. In another embodiment, determining the characteristic includes determining a single value of the characteristic for different areas on the wafer. In one such embodiment, each of the different areas is larger than an area of a patterned feature on the wafer.

In an additional embodiment, generating the output includes generating the output using multiple channels of the inspection system. In one such embodiment, determining the characteristic includes determining the characteristic using the second output generated by one of the multiple channels. Such a method may also include determining a different characteristic of the wafer using the second output generated by another of the multiple channels.

In one embodiment, the method includes performing statistical process control using the characteristic. In another embodiment, the method includes performing inline monitoring of a semiconductor fabrication process using the characteristic to detect excursions in the semiconductor fabrication process. In some embodiments, the method includes determining a standard deviation of the second output for different areas on the wafer and determining if the standard deviations indicate an excursion in a process used to form the wafer.

In an additional embodiment, the method includes determining variation in the second output across the wafer and determining if the variation is associated with a signature of a process tool used to form the wafer. In a further embodiment, the method includes generating a two-dimensional map of the second output across substantially an entire surface of the wafer, determining if an abnormal pattern is present in the two-dimensional map, and if an abnormal pattern is present, determining if the abnormal pattern corresponds to an excursion in a process used to form the wafer.

In one embodiment, the wafer includes an unpatterned wafer or a patterned wafer. In another embodiment, the characteristic includes roughness, reflectivity, thickness, thickness uniformity, polish uniformity, resistivity, or grain size. In some embodiments, the method includes detecting the defects on the wafer using the output. Each of the embodiments of the method described above may include any other step(s) of any other method(s) described herein.

Another embodiment relates to a computer-implemented method for determining a characteristic of a wafer. The method includes acquiring output responsive to light from the wafer generated by an inspection system. The output includes first output corresponding to defects on the wafer and second output that does not correspond to the defects. The method also includes determining the characteristic of the wafer using the second output. This method embodiment may include any other step(s) of any other method(s) described herein.

An additional embodiment relates to a system configured to determine a characteristic of a wafer. The system includes an inspection subsystem configured to illuminate the wafer and to generate output responsive to light from the wafer. The output includes first output corresponding to defects on the wafer and second output that does not correspond to the defects. The system also includes a processor configured to determine the characteristic of the wafer using the second output. The system may be further configured as described herein.

BRIEF DESCRIPTION OF THE DRAWINGS

Other objects and advantages of the invention will become apparent upon reading the following detailed description and upon reference to the accompanying drawings in which.

While the invention is susceptible to various modifications and alternative forms, specific embodiments thereof are shown by way of example in the drawings and will herein be described in detail. It should be understood, however, that the drawings and detailed description thereto are not intended to limit the invention to the particular form disclosed, but on the contrary, the intention is to cover all modifications, equivalents and alternatives falling within the spirit and scope of the present invention as defined by the appended claims.

DETAILED DESCRIPTION OF THE PREFERRED EMBODIMENTS

As used herein, the term "wafer" generally refers to substrates formed of a semiconductor or non-semiconductor material. Examples of such a semiconductor or non-semiconductor material include, but are not limited to, monocrystalline silicon, gallium arsenide, and indium phosphide. Such substrates may be commonly found and/or processed in semiconductor fabrication facilities.

A wafer may include one or more layers formed upon a substrate. For example, such layers may include, but are not limited to, a resist, a dielectric material, and a conductive material. Many different types of such layers are known in the art, and the term wafer as used herein is intended to encompass a wafer including all types of such layers.

One or more layers formed on a wafer may be patterned or unpatterned. In some embodiments, therefore, the wafer includes an unpatterned wafer or a patterned wafer. For example, a wafer may include a plurality of dies, each having repeatable pattern features. Formation and processing of such layers of material may ultimately result in completed devices. Many different types of devices may be formed on a wafer, and the term wafer as used herein is intended to encompass a wafer on which any type of device known in the art is being or will be fabricated.

Although the embodiments of the methods and systems are described herein with respect to a wafer, it is to be understood that the methods and systems described herein may be used for determining one or more characteristics of any specimen that is fabricated using a process for which process monitoring and control based on the characteristic(s) is desirable.

As used herein, the term "characteristic" of a wafer refers to a non-defect related characteristic of a wafer that has a value that is normally measured using a metrology tool. In addition, although the characteristic may have a value that is outside of some predetermined limit thereby rendering the wafer "defective," the characteristic is not related to information about defects that can be determined by an inspection system such as the presence of defects, the location of defects, the number of defects, etc. Examples of "characteristics" of a wafer include, but are not limited to, roughness (e.g., of a surface of the wafer or a film formed on the wafer), reflectivity (e.g., of the wafer or a film formed on the wafer), thickness (e.g., of a film formed on the wafer), thickness uniformity or variation (e.g., of a film such as a dielectric film formed on the wafer), polish uniformity (e.g., of a film formed on the wafer), polish slurry residue (i.e., cleanliness of polishing), resistivity (e.g., of a film formed on the wafer), and grain size (e.g., of a polysilicon film formed on the wafer).

The terms "first output" and "second output" are used herein to differentiate between different portions of output generated by an inspection system. The terms "first" and "second" are not used to indicate temporal, spatial, or preferential characteristics of the output.

Turning now to the drawings, it is noted that the figures are not drawn to scale. In particular, the scale of some of the elements of the figures is greatly exaggerated to emphasize characteristics of the elements. It is also noted that the figures are not drawn to the same scale. Elements shown in more than one figure that may be similarly configured have been indicated using the same reference numerals.

Figure 1:
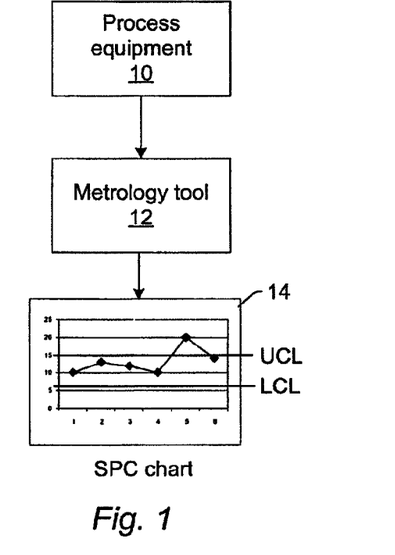
FIG. 1 is a flow chart illustrating one example of a method for monitoring a process based on a characteristic of a wafer.

FIG. 1 illustrates one example of a method for monitoring a semiconductor fabrication process. As shown in FIG. 1, the method includes processing a wafer using process equipment 10. Process equipment 10 may include any appropriate process equipment known in the art of semiconductor manufacturing such as a lithography tool, an etch tool, a chemical-mechanical polishing (CMP) tool, a deposition tool (e.g., a chemical vapor deposition (CVD) tool, a physical vapor deposition (PVD) tool, an atomic layer deposition tool, etc.), a cleaning tool, a plating tool, an ion implantation tool, and a thermal tool (e.g., a rapid thermal annealing tool).

After a wafer has been processed by process equipment 10, one or more characteristics of the wafer are measured by metrology tool 12. Metrology tool 12 may include, for example, an atomic force microscope (AFM) or other scanning probe microscope (SPM) that can be used to measure a characteristic such as surface roughness of the wafer or a film formed on the wafer, a metrology tool such as a spectroscopic ellipsometer configured to measure one or more characteristics such as thickness, thickness uniformity, and reflectivity of a thin film formed on the wafer, and a metrology tool configured to measure one or more electrical characteristics such as resistivity of a thin film formed on the wafer.

After the characteristic(s) of the wafer are measured by metrology tool 12, the measured values of the characteristic(s) can be used for process monitoring and control (e.g., statistical process control (SPC)). For instance, the measured value of a characteristic can be plotted in SPC chart 14. The SPC chart illustrates the value of the characteristic as a function of the measurement number or measurement time, which is illustrated by the dotted line in SPC chart 14. The SPC chart also shows the upper control limit (UCL) and the lower control limit (LCL) for the values of the characteristic. The UCL and the LCL may be determined, for example, based on the design of the devices being formed on the wafer and the degree to which variation in the characteristic affects the devices. SPC chart 14, therefore, provides a graphical representation of variation in the characteristic of the wafer that can be used by engineers or operators in a semiconductor fabrication facility to visually monitor the variation in the characteristic.

In addition, SPC can be performed automatically using the characteristic(s) measured by metrology tool 12 with or without generating SPC chart 14. The method shown in FIG. 1 has proven to be useful for process control and monitoring. For example, many characteristics or "physical quantities" of wafers (surface roughness, reflectivity, film measurement, etc.) used for SPC are measured by metrology tools whose ability to measure the physical quantities has been well established to a certain accuracy.

There are, however, a number of disadvantages to the method shown in FIG. 1. In particular, using measurements of one or more characteristics of wafers performed by a metrology tool for process monitoring and control is disadvantageous because such measurements typically take a relatively long time. Therefore, metrology measurements such as those described above are often not suitable for high sampling of wafers for inline monitoring applications without impacting (e.g., increasing) the cycle time in production. As such, monitoring semiconductor fabrication processes using such measurements may reduce the overall throughput of the processes.

Furthermore, to reduce the effects of the time required for such measurements on the cycle time and throughput of the processes, the measurements are typically performed at only one location or a limited number of locations on the wafer. For example, a critical dimension (CD) measurement may be performed by a metrology tool such as a scanning electron microscope (SEM) at only one spot on the wafer. Performing such measurements across substantially an entire surface of the wafer, however, is generally not an option because the time in which such measurements can be performed is simply too long to be practical. However, as is known in the art, the characteristics of a wafer can vary (sometimes greatly) across the surface of the wafer. As such, performing metrology measurements at only one location or a limited number of locations on the wafer may produce measurements that are not representative of the actual performance of the process, which can lead to inaccurate processing monitoring and control.

The alternatives that are available for decreasing the monitoring frequency of physical quantities of wafers by metrology tools includes reducing the number of measurements performed by the metrology tools, simply not performing the measurements using the metrology tools, and monitoring a diagnostic parameter of a process tool or process equipment instead of using a metrology tool for process monitoring and control. Obviously, each of these alternatives also are disadvantageous for a number of reasons including decreased process monitoring and control capability and less accurate process monitoring and control.

The method and system embodiments described herein, however, can be used to eliminate one or more of these disadvantages. For example, the method and system embodiments described herein can be used to determine a characteristic of a wafer across substantially an entire surface of the wafer (or at least a relatively large portion of the surface of the wafer) relatively quickly. In particular, the method and system embodiments described herein use inspection techniques such as laser- and scattering-based inspection techniques as a proxy for metrology measurements (e.g., surface roughness measurements, reflectivity measurements, thickness measurements, and any other measurements of characteristics described herein). In this manner, the method and system embodiments described herein can advantageously be used for inline process monitoring and control.

In one such example, inline monitoring of a semiconductor fabrication process at production throughput can be achieved using inspection such as laser scattering inspection and correlating the physical quantity or characteristic of the wafers with the output of the inspection system. Therefore, the method and system embodiments described herein allow the use of an inspection system such as the SPx (e.g., SP1 and SP2) systems that are commercially available from KLA-Tencor, San Jose, Calif., as a metrology proxy thereby enabling higher throughput and approximately 100% measurement coverage of the wafer area for physical quantity monitoring. Furthermore, as the number of different films used in semiconductor device manufacturing increases and as the dimensions of semiconductor devices decrease, the surface roughness of the films becomes an important characteristic for monitoring and controlling the process. Therefore, inline monitoring of such characteristics of wafers by the method and system embodiments described herein will only become more important in the future.

The method and system embodiments described herein can also be used to monitor the surface roughness of these films with relatively good accuracy (e.g., with sub-Angstrom surface roughness measurement capability) and relatively high frequency. Relatively high frequency monitoring may involve measuring every wafer in every lot during early development phases of semiconductor manufacturing and may be performed less frequently (e.g., measuring two wafers per lot or two wafers for every four lots) for more mature processes. Obviously, the frequency with which the method and system embodiments described herein are used for inline monitoring and control may be determined based on the semiconductor fabrication process and may be selected by users in a semiconductor fabrication facility.

Figure 2:
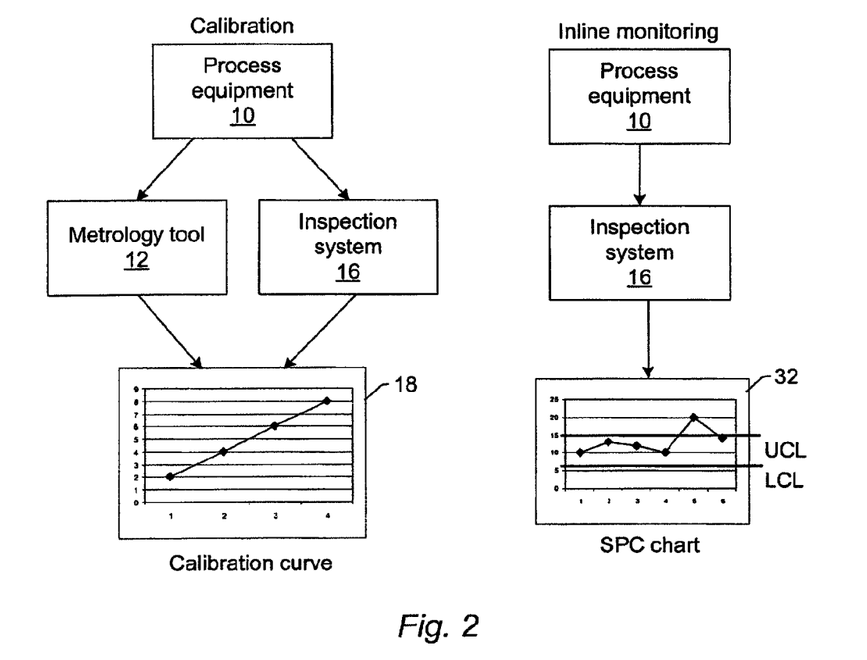
FIG. 2 includes flow charts illustrating one embodiment of a method for setting up a method for monitoring a process based on a characteristic of a wafer and the method for monitoring the process based on the characteristic.

As shown in FIG. 2, one embodiment of a method for setting up (i.e., "calibrating") an embodiment of a method for determining a characteristic of a wafer includes processing a wafer in process equipment 10. Process equipment 10 may include any of the process equipment described above. The method also includes determining one or more characteristics of the wafer using metrology tool 12. Metrology tool 12 may be configured as described above. The one or more characteristics may include any of the characteristic(s) described above. In addition, the method includes generating output responsive to light from the wafer using inspection system 16.

Inspection system 16 may be configured as described herein. For instance, in one embodiment, generating the output using the inspection system includes illuminating the wafer with light produced by a laser. In addition, inspection system 16 may be configured to illuminate the wafer by scanning light across the wafer. In some embodiments, therefore, generating the output using the inspection system includes scanning light across the wafer and generating the output across the wafer. Inspection system 16 may also be configured to detect light scattered from the wafer. In one embodiment, the light from the wafer includes diffusely scattered light.

In an additional embodiment, generating the output using the inspection system includes generating the output across substantially an entire surface of the wafer. Therefore, unlike metrology tools such as AFM tools that scan only a relatively small area (e.g., about 25 microns by about 25 microns) on the wafer to measure a characteristic of the wafer such as surface roughness, the inspection systems described herein can scan across the entire surface of the wafer in a relatively short amount of time (e.g., about 30 seconds). In this manner, the method and system embodiments described herein can measure a characteristic across substantially an entire area of a surface of a wafer in a relatively short time (e.g., about 30 seconds) while measuring the characteristic across the same area on the wafer using a metrology tool can take a relatively long time (e.g., years).

Preferably, more than one wafer is measured by both metrology tool 12 and inspection system 16. For example, the value measured by the metrology tool and the output generated by the inspection system for more than one wafer having approximately the same "real" value of the characteristic may be used to increase the accuracy of the values and output used further in the method. In one such example, the value measured by the metrology tool and the output generated by the inspection system for more than one wafer may be used to generate an average value and an average output, respectively. In addition, more than one wafer, each having a different "real" value of the characteristic, may be acquired by processing the wafers in process equipment 10 with one or more different process parameters and measured by metrology tool 12 and inspection system 16.

The data generated by the method may be used to determine a relationship between the characteristic measured by metrology tool 12 and output from inspection system 16. For instance, the method may include generating calibration curve 18 in which the characteristic measured by metrology tool 12 is plotted as a function of the output of inspection system 16. In this manner, the calibration curve illustrates the correlation between the measured characteristic and the output. The calibration curve or any other data structure defining a relationship between the characteristic and the output may be generated and used in the method embodiments described herein. In this manner, the method described above may be performed for calibrating the output of the inspection system with respect to the measurements of metrology tool 12.

Instead of correlating a characteristic of a wafer measured by a metrology tool to output of an inspection system, the method may be used to determine a correlation between one or more parameters of process equipment 10 and output of inspection system 16. For example, such a correlation may be determined by fixing all but one independent parameter of process equipment 10 and correlating the output of the inspection system such as haze measurements to the parameter. Alternatively, the correlation may be determined by allowing multiple process parameters to vary and using the output generated by multiple channels of the inspection system (which may be configured to detect light from a wafer with different characteristics such as polarization, wavelength, spatial characteristics, etc.) to simultaneously correlate multiple outputs of the inspection system such as multiple haze maps against the independent process parameters. The multiple channels of the inspection system may be configured as described further herein.

The method described above for setting up a method for determining a characteristic of a wafer may be performed prior to using the inspection output for determining a metrology type characteristic of a wafer (i.e., at start up). In addition, the method may be calibrated periodically at relatively low frequency to maintain the accuracy of the method for determining the characteristic of the wafer. For example, the calibration may be performed once a month or once a quarter. The wafers that are used to set up the method may also be used for the periodic calibrations.

One embodiment of a method for determining a characteristic of a wafer is also shown in FIG. 2. The method may include processing a wafer in process equipment 10, which may include any of the process equipment described above. The method also includes generating output responsive to light from the wafer using inspection system 16. The output includes first output corresponding to defects on the wafer and second output that does not correspond to the defects. In particular, if defects are present on the wafer, the defects may alter the portion of the output generated by the inspection system at the positions of the defects.

Figure 3:
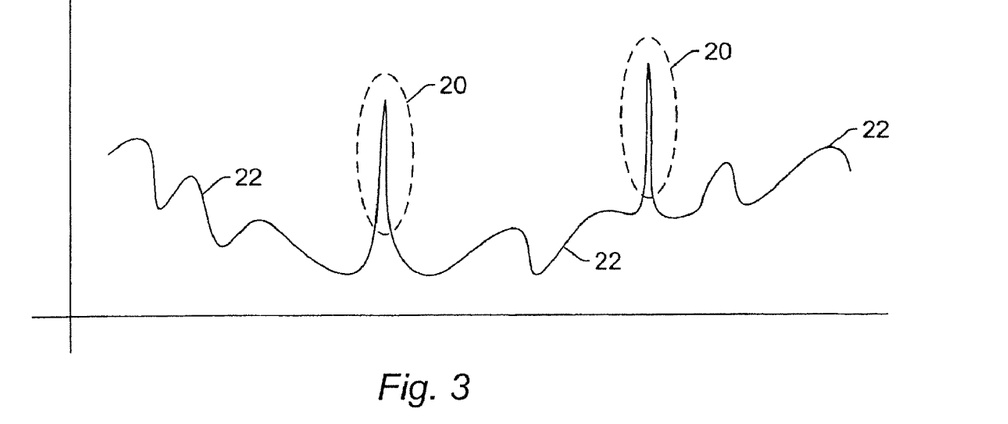
FIG. 3 is a plot illustrating one example of output responsive to light from a wafer generated by an inspection system.

For instance, FIG. 3 illustrates a plot of an example of output of an inspection system (e.g., the wafer surface scattering signal is plotted as a function of position on the wafer). As further shown in FIG. 3, output of an inspection system includes first output 20 corresponding to defects such as particulate defects on the wafer. First output 20 may be identified by applying a threshold or other algorithm to the output. For instance, the output may be compared to a relatively high threshold such that output corresponding to defects can be discriminated from output that corresponds to noise or light scattered from the surface of the wafer. The output also includes second output 22 that includes all of the output that does not correspond to the defects.

The output of the inspection system, therefore, may include a relatively large amount of data for a wafer. Normally, the output corresponding to the defects is the output of interest for inspection, and the output that does not correspond to defects is considered noise, nuisance, or background. For example, the output corresponding to the defects may be stored and further processed (e.g., to form a defect map such as a light point defect (LPD) map, to determine locations of the defects on the wafer, etc.). All other output generated by the inspection system is considered noise for the purposes of inspection and may be discarded since it does not correspond to defects. Much work in the inspection field has been devoted to suppressing the output that does not correspond to defects to increase the sensitivity of defect detection.

In the embodiments described herein, however, this second output may be used as a proxy for a characteristic of the wafer. In particular, in the method and system embodiments described herein, this "noise" in the output is used to determine a characteristic of a wafer. In this manner, unlike most methods and systems that are designed to suppress this noise in the output, the method and system embodiments described herein advantageously use this noise as a proxy for a characteristic of the wafer. In other words, output responsive to the light scattered from the surface of the wafer may be acquired and sampled in some manageable way such that it can be processed as described further herein. Furthermore, determining the characteristic using only the second output instead of all of the output of the inspection system increases the accuracy with which the characteristic is determined.

The method also includes determining the characteristic of the wafer using the second output. In one embodiment, determining the characteristic of the wafer includes determining the characteristic of the wafer using the second output and a predetermined correlation between the second output and the characteristic. For example, if "calibration" is performed as shown in FIG. 2, the characteristic of the wafer may be determined using the second output in combination with calibration curve 18. Therefore, when determining a characteristic of a wafer using an inspection system such as a laser scattering inspection system, the measurements of the inspection system may be reported in physical units such as roughness in Angstroms, sheet resistance in Ohms, and film thickness in Angstroms instead of the typical manner in which measurements performed by inspection systems are reported (e.g., scattering units such as ppm or "total integrated scatter signal") for inspection applications.

Therefore, as shown by comparing the methods of FIGS. 1 and 2 for determining a characteristic of a wafer, the method of FIG. 2 uses output of an inspection system as a metrology proxy for measurements that are normally performed by a metrology tool. Since the characteristic or physical quantity of the wafer can be determined using an inspection system and an appropriate correlation or other data processing described further herein and since inspection systems can acquire data for a wafer much quicker than a metrology tool, the methods and systems described herein can measure the physical quantity of the wafer much faster than traditional metrology equipment. In addition, unlike other methods that have been attempted for indirectly measuring a characteristic of a wafer (e.g., determining a surface roughness from a haze measurement) that involve relatively time consuming and complicated modeling, the method and system embodiments described herein can determine the characteristic of the wafer from a relatively simple correlation or calibration of the output and the characteristic.

As described above, generating the output using the inspection system may include generating the output across substantially an entire surface of the wafer. In one such embodiment, determining the characteristic includes determining the characteristic using the second output generated across substantially the entire surface of the wafer. In this manner, the characteristic may be determined using all of the output generated for the wafer by the inspection system except for the output corresponding to the defects. As such, the characteristic of the wafer may be measured across substantially an entire surface of the wafer.

In another embodiment, determining the characteristic includes determining a value for the second output across an area on the wafer and determining the characteristic from the value. In one such embodiment, the area on the wafer across which the second output is generated and used to determine the value may be substantially an entire area of a surface on the wafer. In this manner, the value may be determined using all of the output generated for the wafer by the inspection system except for the output corresponding to the defects. The value determined for the second output may include, for example, an average, a mean, a median, a standard deviation or any other appropriate value for the second value. In this manner, the characteristic of the wafer determined by this value may be an average, a mean, a median, a standard deviation, etc. of the characteristic. However, such values of the characteristic across an area on the wafer (e.g., substantially an entire area of a surface of the wafer) may be determined in any other manner.

In an additional embodiment, determining the characteristic of the wafer includes determining variation in the second output across the wafer and determining the characteristic from the variation. In a further embodiment, determining the characteristic includes generating a two-dimensional map of the second output across substantially an entire surface of the wafer and determining the characteristic from the two-dimensional map. In other words, the second output generated by the inspection system provides a volume of data that can be used to generate a graphical representation that illustrates the entire wafer and the variation in the characteristic across the wafer. In this manner, the two-dimensional map of the second output may be used to identify surface anomalies of interest (AOI).

In some embodiments, determining the characteristic includes determining a value for the second output across different areas on the wafer and determining the characteristic for the different areas using the values. In another embodiment, determining the characteristic includes determining a single value of the characteristic for different areas on the wafer. In this manner, the method and system embodiments described herein can use the output of an inspection system to find spatial variation in a characteristic of a wafer.

Figure 4:
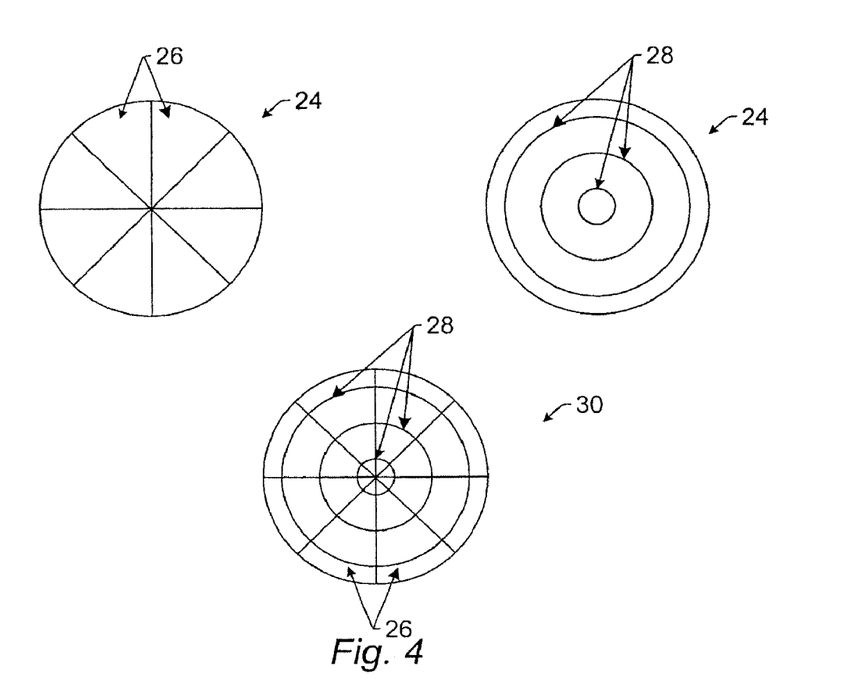
FIG. 4 is a schematic diagram illustrating a top view of various embodiments of different areas on a wafer.

The different areas on the wafer may be defined by different polar coordinates. Examples of such different areas are shown in FIG. 4. In particular, the area of wafer 24 may be divided into different areas 26 that are defined by different angular coordinates or different fixed angles. Substantially the entire area of a surface of wafer 24 may be included in different areas 26, or different areas 26 may span only a portion of the entire surface of the wafer. Although a particular number of different areas 26 are shown in FIG. 4, it is to be understood that the wafer area may be separated into any suitable number of such different areas.

Alternatively, the different areas on the wafer may be defined by different radial coordinates or different fixed radii. In this manner, the different areas on the wafer may have generally concentric circle shapes. One example of such different areas is shown in FIG. 4. In particular, the area of wafer 24 may be divided into different areas 28. Substantially the entire area of a surface of the wafer may be included in different areas 28, or different areas 28 may span only a portion of the entire surface of the wafer. Although a particular number of different areas 28 are shown in FIG. 4, it is to be understood that the wafer area may be separated into any suitable number of such different areas.

In addition, both different areas 26 and 28 may be defined across the area of a single wafer. For example, as shown in FIG. 4, wafer 30 may be separated into different areas 26 and 28. In this manner, the characteristic of the wafer may be determined across different areas that overlap to some extent on the wafer. Determining the characteristic for the overlapping areas may be advantageous when it is desirable to examine the characteristic for variations in different spatial arrangements across a single wafer.

Each of the different areas is larger than an area of a patterned feature on the wafer. For example, the different areas on the wafer may have lateral dimensions of about 1 micron by about 1 micron. In another example, the different areas on the wafer may have lateral dimensions of about 25 microns by about 25 microns. In this manner, the characteristic may be determined for different areas on the wafer that have sizes that are approximately equal to the size of a reticle field printed on the wafer. The lateral dimensions of all, some, or none of the different areas may be the same or different.

Unlike metrology tools that measure a characteristic of an area on the wafer occupied by a single patterned feature, the value of the characteristic determined by the method and system embodiments described herein may be a value that represents the characteristic across an area on the wafer that is much larger than an area of a patterned feature. As such, the effect of any single patterned feature on the output of the inspection system may be reduced or "averaged out." In this manner, unlike metrology tools that are configured to measure a characteristic of a wafer at one or more discrete locations on the wafer, the inspection systems described herein may be used to process the optical characteristics of the wafer (e.g., the second output) on average and to determine the characteristic of the wafer as an average. Therefore, the single value of the characteristic determined for each of the different areas may be an average value of the characteristic across each of the different areas. Accordingly, the characteristics determined by the embodiments described herein are determined on a macro level, while the characteristics of the wafer determined by metrology tools are determined on a micro level.

In a further embodiment, generating the output includes generating the output using multiple channels of the inspection system. In one such embodiment, determining the characteristic includes determining the characteristic using the second output generated by one of the multiple channels. Such an embodiment may also include determining a different characteristic of the wafer using the second output generated by another of the multiple channels. In this manner, by scanning the wafer using an inspection system that has multiple channels, the method and system embodiments described herein can be used to determine multiple characteristics of the wafer. The multiple characteristics may be determined simultaneously. The multiple channels of the inspection system may be configured as described further herein.

The method embodiments described herein may also include detecting defects on the wafer using the output. In particular, as described above, the first output corresponding to defects may be identified in the output generated by the inspection system. The portion of the output that does not correspond to defects may be used as described herein to determine the characteristic of the wafer. Although the first output is not used to determine the characteristic of the wafer, the first output may not be discarded and may, therefore, be used for other purposes. For example, since the first output corresponds to defects and is identified to distinguish the first output from the second output, identifying the first output may also be used to identify and detect defects on the wafer. In this manner, the method and system embodiments described herein may be used to simultaneously detect defects on a wafer and determine a characteristic of the wafer.

As described above, the method embodiments may include generating a two-dimensional map of the second output across an area or substantially an entire surface of the wafer. In this manner, the two-dimensional map may represent an "image" of the area of the wafer or substantially the entire surface of the wafer. As described further above, the "image" represents the low frequency components of the total light scattering signal originating from interaction of the laser with the surface or interfacial material characteristics at varying layer thicknesses and optical properties. In some cases, a continuous and extended area defect can be extensive enough to alter this background haze. In this manner, in addition to detecting defects on the wafer from the first output as described above, the "image" allows analysis of the signature (e.g., a haze signature) on the wafer surface to identify continuous or extended area defects on the wafer that may otherwise be easily overlooked. Some channels of an inspection system may be more sensitive to such defects than other channels. For instance, the normal (narrow) channel of the inspection system described further below may be the most sensitive channel of this system for identifying continuous and extended area defects. In this manner, only a portion of the output of the system may be used for detecting such defects. Detecting such defects may be particularly important in applications such as resist coating layer inspection since such defects may represent small variations in the uniformity of the resist coating layer prior to exposure that in turn can lead to subsequent variation in line width due to the variation in the pre-exposure resist coating layer or a missing pattern in the worst case.

The measurements of the inspection system described herein may be used for process excursion monitoring. In addition, the metrology proxy measurements performed by the inspection system may be used for relatively frequent monitoring of the process because these measurements may be performed much quicker than the measurements performed by metrology tools. In one embodiment, the method includes performing SPC using the characteristic. Performing SPC is generally shown in FIG. 2 by SPC chart 32, which may be configured as described above. However, it is to be understood that SPC may be performed in any suitable manner known in the art. In addition, if more than one characteristic of the wafer is determined in the embodiments described herein, one or more of the characteristics of the wafer can be used to perform SPC. In another embodiment, the method includes performing inline monitoring of a semiconductor fabrication process using the characteristic to detect excursions in the semiconductor fabrication process. In one such embodiment, the method includes determining a standard deviation of the second output for different areas on the wafer and determining if the standard deviations indicate an excursion in a process used to form the wafer.

If a process excursion is identified by the method and system embodiments described herein, the method and system embodiments may identify the wafer on which the process excursion was detected as a candidate for metrology. In this manner, the characteristic of a wafer on which a process excursion was detected may be verified or measured using a metrology tool, and the value of the characteristic determined by the metrology tool may be used to determine the appropriate correction for the process.

In some embodiments, the method includes determining variation in the second output across the wafer and determining if the variation is associated with a signature of a process tool used to form the wafer. For example, a wafer that has been processed by a deposition tool may have a characteristic that varies across the wafer due to the chuck of the deposition tool. In addition, the variation in the characteristic of the wafer due to the chuck may be detected using the output (e.g., haze measurements) of the inspection system. The variation in the second output may be determined as a standard deviation in the second output. In addition, the standard deviation in the second output may be determined for different areas on the wafer. The different areas may be defined as described further herein. The standard deviations for each of the different areas may be compared to a predetermined threshold or limit for the standard deviation. In this manner, the standard deviation values that are greater than the threshold or limit may be flagged or identified as indicating a process excursion that may be associated with the signature of the process tool.

In a further embodiment, the method includes generating a two-dimensional map of the second output across substantially an entire surface of the wafer, determining if an abnormal pattern is present in the two-dimensional map, and if an abnormal pattern is present, determining if the abnormal pattern corresponds to an excursion in a process used to form the wafer. The abnormal patterns in the two-dimensional map may be identified using any suitable method and/or algorithm known in the art. The abnormal patterns that can be detected using such a method include, but are not limited to, a chuck imprint of a deposition tool (e.g., a CVD deposition tool), poor or non-uniform etch, a "swirl" in copper formed by an electro-chemical deposition (ECD) process, a pattern corresponding to a showerhead of a plasma CVD tool that uses tetraethoxy silane (TEOS) gas, thickness variation, wet cleaning problems, and slurry residue. In this manner, the method and system embodiments described herein may be used to identify spatial variation in a characteristic of a wafer and to use the spatial variation as an indicator of process excursions.

The method may also include storing results of the determining step in a storage medium. The results of the determining step may include any of the results described herein. In addition, the storing step may include storing results of the determining step in addition to any other results of any steps of any method embodiments described herein. The results may be stored in any manner known in the art. In addition, the storage medium may include any storage medium described herein or any other suitable storage medium known in the art. After the results have been stored, the results can be accessed in the storage medium and used by any of the method or system embodiments as described herein. Furthermore, the results may be stored "permanently," "semi-permanently," temporarily, or for some period of time. For example, the storage medium may be random access memory (RAM), and the results of the selecting step may not necessarily persist indefinitely in the storage medium.

Figure 5:
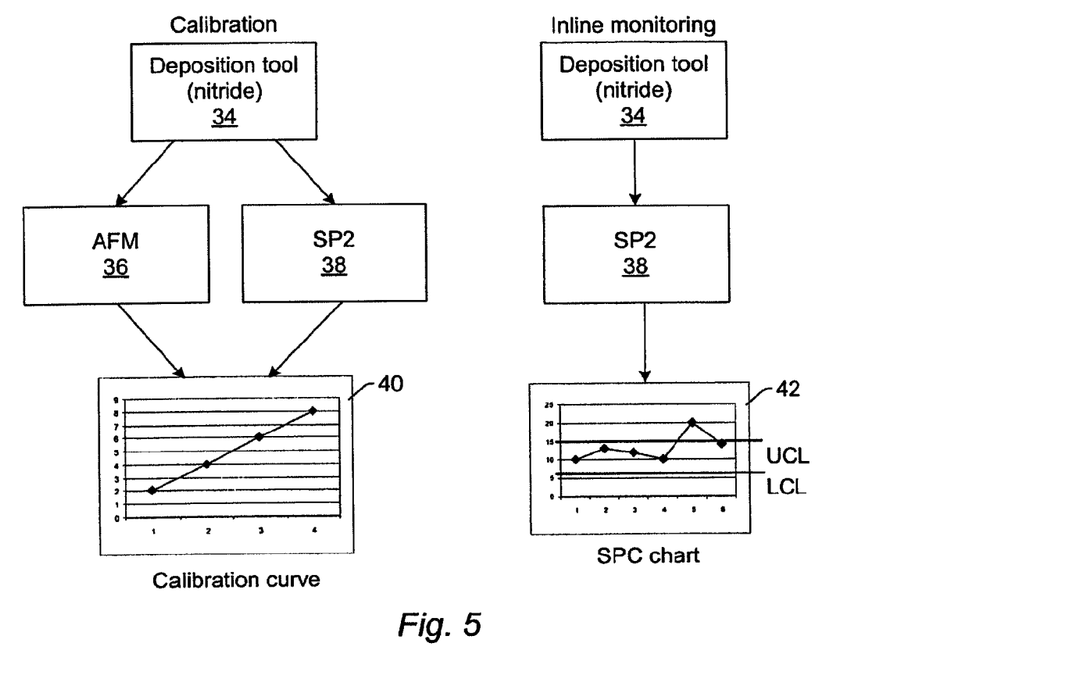
FIG. 5 includes flow charts illustrating another embodiment of a method for setting up a method for monitoring a process based on a characteristic of a wafer and the method for monitoring the process based on the characteristic.

FIG. 5 illustrates one particular implementation of an embodiment of a method for setting up a method for determining a characteristic of a wafer and one particular implementation of an embodiment of such a method for determining the characteristic of the wafer. As shown in FIG. 5, setting up the method or "calibration" includes processing one or more wafers in deposition tool 34. Deposition tool 34 may, in this example, be used to form a nitride layer on the one or more wafers. However, deposition tool 34 may be configured to deposit or form any suitable layer known in the art of semiconductor fabrication on the wafer(s). The deposition tool may be used to form the layer having substantially the same characteristics (e.g., thickness) on more than one wafer. In addition, the deposition tool may be used to form layers having different characteristics (e.g., thickness) on more than one wafer.

As shown in FIG. 5, one or more characteristics of wafer(s) processed by deposition tool 34 may be measured by AFM 36. AFM 36 may be used to measure a surface roughness of the nitride or other layer formed on the wafer(s). AFM 36 may include any suitable AFM known in the art, and many suitable AFM systems are commercially available. Wafer(s) processed by deposition tool 34 and measured by AFM 36 are also measured using an inspection system such as SP2 system 38 that is commercially available from KLA-Tencor. However, the inspection system used to measure the wafer(s) may include any suitable inspection system known in the art, and many suitable inspection systems such as the SP1 and AIT family of tools are commercially available from KLA-Tencor. The inspection system may be configured to measure the wafer by generating output responsive to the light from the wafer according to any of the embodiments described herein.

The measurements performed on the wafer(s) by AFM 36 and SP2 system 38 may be analyzed and/or processed to determine a correlation between the different measurements. For example, as shown in FIG. 5, the method may include generating calibration curve 40 that describes a correlation between the measurements of the wafer(s) performed by AFM 36 and SP2 system 38. However, any other suitable data structures (e.g., a look up table, a mathematical function, or an algorithm) may be used to describe the relationship between the measurements performed by AFM 36 and SP2 system 38. In addition, measurements performed on multiple wafers having substantially the same characteristics may be used to create the correlation thereby increasing the accuracy of the correlation. Furthermore, measurements performed on multiple wafers having different characteristics may be used to create the correlation across different possible values of the characteristic(s) thereby increasing the accuracy of the correlation across a range of possible values. The "calibration" of the SP2 system may be performed as shown in FIG. 5 at relatively low frequency (e.g., at start up and for periodic maintenance (PM)). The "calibration" method shown in FIG. 5 may include any other step(s) of any other method(s) described herein.

As further shown in FIG. 5, the method for determining a characteristic of the wafer may be used for inline monitoring. During inline monitoring, wafers may be processed by deposition tool 34 to form a nitride or other suitable layer on the wafers. Wafers on which the nitride or other layer is formed may then be measured by SP2 system 38. Output of the SP2 system in combination with calibration curve 40 or other data structure described above may be used to determine one or more characteristics of the wafers. For example, output of the SP2 system may be used in combination with calibration curve 40 to determine the surface roughness of the layers formed on the wafers.

The characteristic(s) of the wafers determined from the output of the SP2 system and the calibration curve may then be used for SPC of the process performed by deposition tool 34. For example, SPC of the process performed by the deposition tool may be performed by generating SPC chart 42, which may be configured and used as described above. However, SPC of the deposition process may be performed in any suitable manner known in the art. Since the output of the SP2 system can be generated relatively quickly and the characteristic of the wafers can be determined relatively quickly from the output, the method shown in FIG. 5 may be used for relatively frequent monitoring of the deposition process (e.g., daily monitoring). In addition, since the output of the SP2 system can be generated relatively quickly across substantially an entire area of a surface of the wafer, relatively frequent monitoring of the process may be performed using full wafer coverage measurements of the characteristic. The embodiments of the methods shown in FIG. 5 may include any other step(s) of any other method(s) described herein. In addition, the embodiments of the methods shown in FIG. 5 have all of the advantages of the method embodiments described above.

Figure 6:
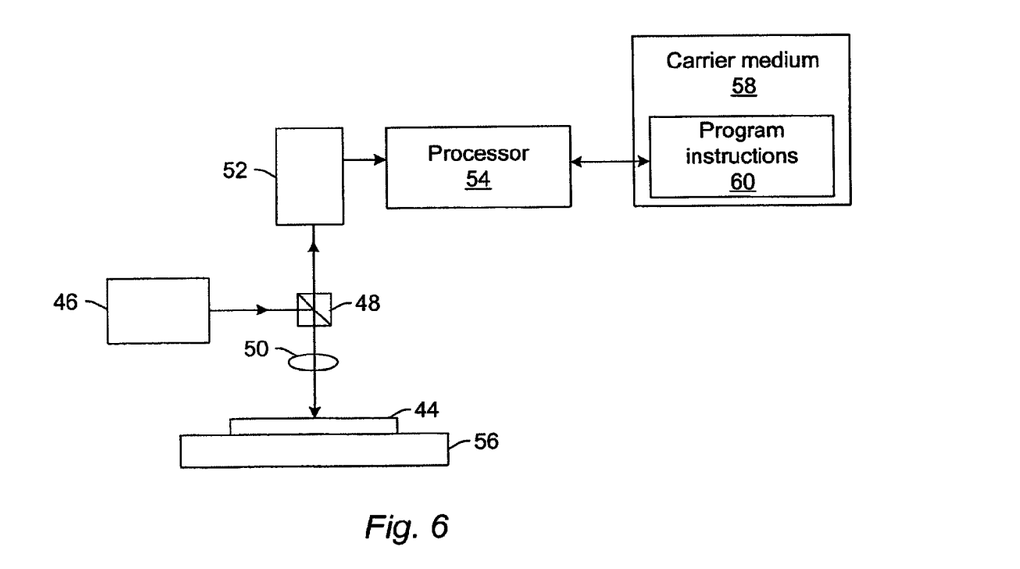
FIGS. 6-7 are schematic diagrams illustrating a cross-sectional view of various embodiments of a system configured to determine a characteristic of a wafer.

FIG. 6 illustrates one embodiment of a system configured to determine a characteristic of a wafer. The system includes an inspection subsystem that is configured to illuminate wafer 44 and to generate output responsive to light from the wafer. The output includes first output corresponding to defects on the wafer and second output that does not correspond to the defects. For example, the inspection subsystem includes light source 46. Light source 46 may include any suitable light source known in the art. Light generated by light source 46 is directed to beam splitter 48. Beam splitter 48 is configured to direct the light generated by light source 46 to objective 50. Objective 50 is configured to focus the light onto wafer 44. In this manner, the light source, beam splitter, and objective of the inspection subsystem are configured to illuminate wafer 44. Beam splitter 48 and objective 50 may include any suitable optical components known in the art. In one embodiment, light source 46 includes a laser. In this manner, the inspection subsystem may be configured to illuminate the wafer with light produced by a laser.

Light specularly reflected from wafer 44 is collected by objective 50, directed by objective 50 to beam splitter 48, and passed through beam splitter 48 to detector 52. Detector 52 may include any suitable detector known in the art. Since light detected by detector 52 includes light specularly reflected from wafer 44, the inspection subsystem shown in FIG. 5 is configured as a bright field inspection subsystem. In addition, since the systems described herein are preferably configured to determine the characteristic of the wafer across a relatively large area on the wafer (e.g., substantially an entire area of a surface of the wafer) for the purposes of process excursion monitoring, the inspection subsystem may be configured to detect the light specularly reflected across a relatively large area on the wafer and at relatively low resolution. In this manner, light source 46, beam splitter 48, and objective 50 may be configured to illuminate a relatively large area or spot on wafer 44. In addition, detector 52 may be a relatively low quality imaging detector or a non-imaging detector capable of measuring only an intensity of the light reflected from the wafer.

The inspection subsystem shown in FIG. 6 may include any other suitable components or devices known in the art. For example, as shown in FIG. 6, the inspection subsystem may include stage 56 on which wafer 44 may be disposed during measurements by the inspection subsystem. Stage 56 may include any suitable mechanical or robotic assembly known in the art. Stage 56 may be configured to move wafer 44 during measurements performed by the inspection subsystem such that the inspection subsystem generates output responsive to light from the wafer by scanning light across the wafer and generating the output across the wafer. In addition, the inspection subsystem may be configured to generate the output responsive to the light from the wafer by generating the output across substantially an entire area of the surface of the wafer.

Detector 52 may generate output that can be used as described further herein. In addition, the output generated by detector 52 may include first output corresponding to defects on wafer 44 and second output that does not correspond to the defects. The system also includes processor 54 configured to determine the characteristic of the wafer using the second output. For example, processor 54 may be coupled to detector 52 in any manner known in the art (e.g., via a transmission medium that may include "wired" and "wireless" portions). In this manner, processor 54 may be configured to receive output generated by detector 52.

Processor 54 may be configured to determine the characteristic of the wafer using the second output generated by detector 52 as described further herein. For example, in one embodiment, processor 54 is configured to determine the characteristic using the output generated across substantially the entire surface of the wafer. In another embodiment, processor 54 is configured to determine the characteristic of the wafer using the second output and a predetermined correlation between the second output and the characteristic. In an additional embodiment, the processor is configured to determine a value for the second output across an area on the wafer and to determine the characteristic from the value. In some embodiments, the characteristic is an average characteristic across an area on the wafer.

In another embodiment, processor 54 is configured to determine variation in the second output across the wafer and to determine the characteristic from the variation. In one such embodiment, the processor may be configured to determine a graininess of a film or films deposited on the wafer by determining if pixels of data in the second output have values that fall into a mean/range space using segmented auto thresholding (SAT) and estimating the graininess of the film from the number of pixels that have such values. In a further embodiment, processor 54 is configured to generate a two-dimensional map of the second output across substantially an entire surface of the wafer and to determine the characteristic of the wafer from the two-dimensional map. In some embodiments, processor 54 is configured to determine a value for the second output across different areas on the wafer and to determine the characteristic for the different areas using the values. In an additional embodiment, the processor is configured to determine a single value of the characteristic for different areas on the wafer. Each of the different areas is larger than an area of a patterned feature on the wafer.

Processor 54 may be configured to perform any other step(s) of any other method(s) described herein. For example, in one embodiment, processor 54 is configured to perform SPC using the characteristic. In another embodiment, processor 54 is configured to perform inline monitoring of a semiconductor fabrication process using the characteristic to detect excursions in the process. In some embodiments, processor 54 is configured to determine a standard deviation of the second output for different areas on the wafer and to determine if the standard deviations indicate an excursion in a process used to form the wafer. In a further embodiment, the processor is configured to generate a two-dimensional map of the second output across substantially an entire surface of the wafer, to determine if an abnormal pattern is present in the two-dimensional map, and if an abnormal pattern is present, to determine if the abnormal pattern corresponds to an excursion in a process used to form the wafer. In an additional embodiment, the processor is configured to detect defects on the wafer using the output. Each of the steps described above may be performed by the processor as described further herein.

Processor 54 may take various forms, including a personal computer system, mainframe computer system, workstation, image computer, parallel processor, or any other suitable device known in the art. In general, the term "computer system" may be broadly defined to encompass any device having one or more processors, which executes instructions from a memory medium. The embodiments of the system shown in FIG. 6 have all of the advantages of the methods described above.

In some embodiments, the system shown in FIG. 6 also includes carrier medium 58. Program instructions for implementing methods such as those described herein may be transmitted over or stored on the carrier medium. In particular, carrier medium 58 includes program instructions 60 executable on processor 54 for performing one or more steps of the methods described herein. For example, in one embodiment, carrier medium 58 includes program instructions 60 executable on a computer system such as processor 54 for performing a method for determining a characteristic of wafer 44. Although the processor and carrier medium are shown in FIG. 6 as coupled to an inspection subsystem, it is to be understood that the processor and/or carrier medium may be configured as separate "stand-alone" components. Such stand-alone components may, however, be coupled to an inspection system (e.g., by a transmission medium that may include "wired" and "wireless" portions) such that the components can receive output generated by the inspection system.

The computer-implemented method includes acquiring output responsive to light from the wafer generated by an inspection system. Acquiring the output may be performed by processor 54 as described further above. The output includes first output corresponding to defects on the wafer and second output that does not correspond to the defects. In some embodiments, the method includes identifying the first and second output in the output acquired from the inspection system. The first and second output may be identified as described further above.

The method also includes determining the characteristic of the wafer using the second output. Determining the characteristic of the wafer may be performed as described further herein. For example, in one embodiment, determining the characteristic includes determining the characteristic of the wafer using the second output generated across substantially an entire surface of the wafer. In another embodiment, determining the characteristic includes determining the characteristic of the wafer using the second output and a predetermined correlation between the second output and the characteristic. In an additional embodiment, determining the characteristic of the wafer includes determining a value for the second output across an area on the wafer and determining the characteristic from the value. In some embodiments, the characteristic is an average characteristic across an area on the wafer.

In a further embodiment, the method includes determining variation in the second output across the wafer and determining the characteristic from the variation. In another embodiment, determining the characteristic includes generating a two-dimensional map of the second output across substantially an entire surface of the wafer and determining the characteristic from the two-dimensional map. In some embodiments, determining the characteristic includes determining a value for the second output across different areas on the wafer and determining the characteristic for the different areas using the values. In an additional embodiment, determining the characteristic includes determining a single value of the characteristic for different areas on the wafer. Each of the different areas is larger than an area of a patterned feature on the wafer.

In a further embodiment, the output may be generated by multiple channels of the inspection system. In one such embodiment, determining the characteristic includes determining the characteristic using the second output generated by one of the multiple channels. Such an embodiment may also include determining a different characteristic of the wafer using the second output generated by another of the multiple channels.

The computer-implemented method may include any other step(s) of any other method(s) described herein. For example, in one embodiment, the computer-implemented method includes performing SPC using the characteristic. In another embodiment, the method includes performing inline monitoring of a semiconductor fabrication process using the characteristic to detect excursions in the semiconductor fabrication process. In an additional embodiment, the method includes determining a standard deviation of the second output for different areas on the wafer and determining if the standard deviations indicate an excursion in a process used to form the wafer.

In one embodiment, the computer-implemented method includes determining variation in the second output across the wafer and determining if the variation is associated with a signature of a process tool used to form the wafer. In some embodiments, the method includes generating a two-dimensional map of the second output across substantially an entire surface of the wafer, determining if an abnormal pattern is present in the two-dimensional map, and if an abnormal pattern is present, determining if the abnormal pattern corresponds to an excursion in a process used to form the wafer. In a further embodiment, the computer-implemented method includes detecting defects on the wafer using the output. Each of the steps of the computer-implemented method described above may be performed as described further herein. Each of the embodiments of the computer-implemented method described above has all of the advantages of the methods described above.

The embodiments of the carrier medium may include program instructions executable on a computer system of any other inspection system that is or can be configured as described herein. The carrier medium may be a transmission medium such as a wire, cable, or wireless transmission link. The carrier medium may also be a storage medium such as a read-only memory, a random access memory, a magnetic or image acquisition disk, or a magnetic tape.

The program instructions may be implemented in any of various ways, including procedure-based techniques, component-based techniques, and/or object-oriented techniques, among others. For example, the program instructions may be implemented using Matlab, Visual Basic, ActiveX controls, C, C++ objects, C#, JavaBeans, Microsoft Foundation Classes ("MFC"), or other technologies or methodologies, as desired.

Figure 7:
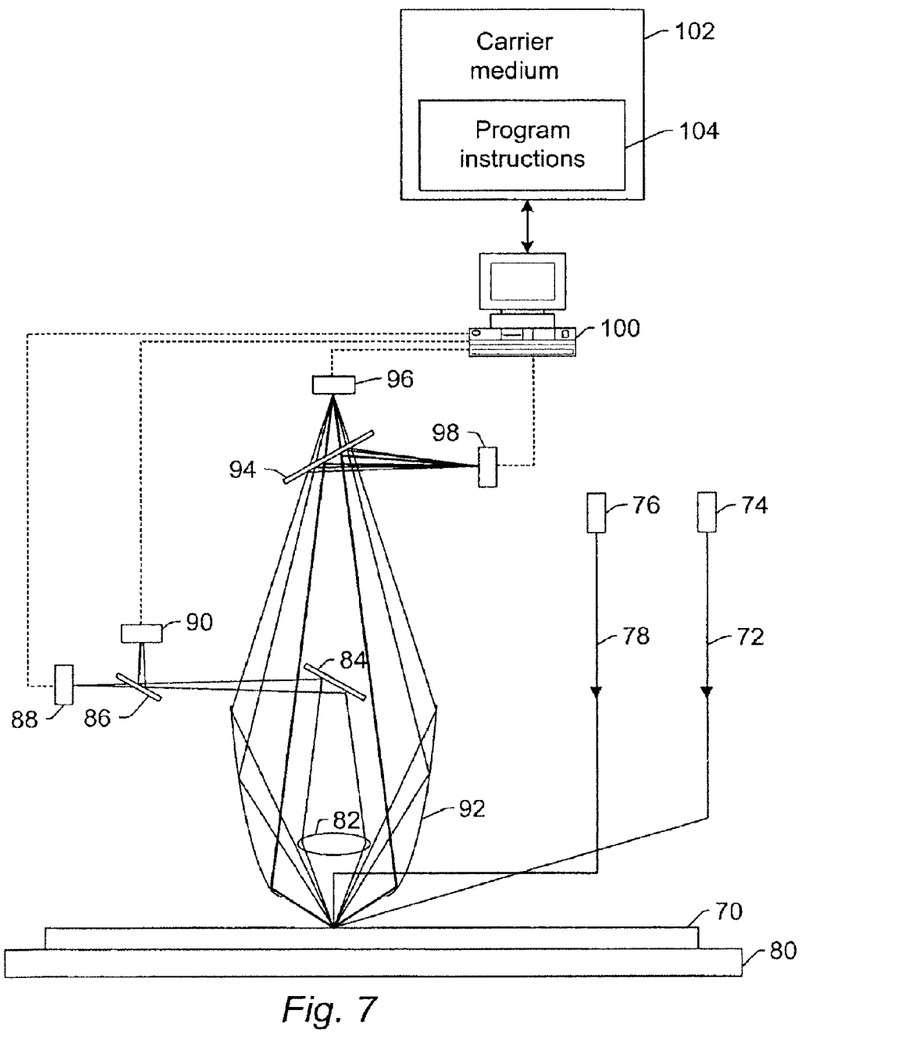

Another embodiment of a system that is configured to inspect a wafer is illustrated in FIG. 7. The system shown in FIG. 7 is configured for unpatterned wafer inspection and is based on the SP1-TB1 system, which is commercially available from KLA-Tencor. This inspection system is described in more detail in U.S. Pat. No. 6,538,730 to Vaez-Iravani et al., which is incorporated by reference as if fully set forth herein. The system shown in FIG. 7 may be further configured as described in this patent for patterned and unpatterned wafer inspection. For the sake of clarity, some of the components and details of the system have been omitted from FIG. 7 and the corresponding description presented herein. In addition, U.S. Pat. No. 6,538,730 is related to U.S. Pat. Nos. 6,201,601 to Vaez-Iravani et al. and 6,271,916 to Marxer et al., which are also incorporated by reference as if fully set forth herein. The system shown in FIG. 7 may be further configured as described in these patents.

The system shown in FIG. 7 includes an inspection subsystem. The inspection subsystem is configured to illuminate the wafer and to generate output responsive to light from the wafer. The output includes first output corresponding to defects on the wafer and second output that does not correspond to the defects.

The inspection subsystem includes an illumination subsystem. The illumination subsystem may be configured to generate light 72. For instance, the illumination subsystem may include light source 74, which is configured to generate light 72. The illumination subsystem is configured to direct light 72 to wafer 70 at an oblique angle of incidence. The illumination subsystem may include a number of optical components (not shown) positioned in a path of light 72 such as folding mirror(s), beam splitter(s), polarizing component(s), filter(s), and lenses. The oblique angle of incidence may vary depending on, for example, the characteristics of the light and the characteristics of the wafer. One suitable angle of incidence may be about 70° from normal to the upper surface of the wafer.

The illumination subsystem also includes light source 76. Light source 76 is configured to generate light 78, which is directed by the illumination subsystem to wafer 70 at a substantially normal angle of incidence. The illumination subsystem may include a number of optical components (not shown) positioned in the path of light 78. These optical components may include any of those described above.

Light sources 74 and 76 may include any suitable light sources known in the art such as lasers. In one embodiment, therefore, the inspection subsystem is configured to illuminate the wafer with light produced by one or more lasers. In a different embodiment, the system may include a single light source (not shown) that is used to provide light for both oblique and normal illumination as described further above. For example, a single light source such as a multi-wavelength laser may be coupled to a beam splitter (not shown). The beam splitter may be configured to split the light from the laser into separate beams having different wavelengths, one of which is used for normal illumination and the other of which is used for oblique illumination. The illumination subsystem may include any other suitable combination of a single light source and beam multiplier(s) known in the art.

Wafer 70 is supported on stage 80, which may be rotated and translated such that light 72 and 78 illuminates an area or spot on the wafer that moves in a spiral path. Alternatively, light 72 and 78 may be scanned over the wafer in any manner known in the art to trace the spiral path or another type of scan path across the wafer. In this manner, the inspection subsystem may be configured to illuminate the wafer by scanning light across the wafer and to generate the output as described further herein across the wafer. In addition, the inspection subsystem may be configured to scan the light across substantially an entire surface of the wafer and to generate the output as described further herein across substantially the entire surface of the wafer.

Illumination of the wafer will cause scattering of the light from the wafer. In addition, both oblique incidence light and normal incidence light may be scattered from the wafer. The inspection subsystem shown in FIG. 7 includes a detection subsystem that is configured to collect light scattered from the wafer and to generate output responsive to light from the wafer. The output can be used to determine a characteristic of the wafer as described further herein.

The detection subsystem includes lens collector 82, mirror 84, beam splitter 86, and detectors 88 and 90, which form a "narrow" channel of the detection subsystem. In other words, light scattered from the illuminated area on the wafer along directions relatively close to normal to the surface of the wafer is collected and focused by lens collector 82. In this manner, lens collector 82 collects light scattered from the wafer at relatively "narrow" scattering angles. The light from the wafer collected by lens collector 82 may include diffusely scattered light. Lens collector 82 directs the collected light to mirror 84, which directs the light to beam splitter 86. Beam splitter 86 is configured to direct one portion of the light to detector 88 and the other portion of the light to detector 90. One detector may be used to detect light scattered at relatively narrow angles due to illumination by the normal incidence beam, and the other detector may be used to detect light scattered at relatively narrow angles due to illumination by the oblique incidence beam. Detectors 88 and 90 may include any suitable detectors known in the art (e.g., PMTs). In addition, detectors 88 and 90 may be similarly or differently configured. The narrow channel portion of the detection subsystem may include any other optical components (not shown) known in the art. For example, one or more spectral filtering components (e.g., bandpass filters) may be placed in the path of the collected light between beam splitter 86 and each of detectors 88 and 90. In addition, a spatial filter may be included in the narrow channel portion of the detection subsystem to prevent the specular reflection of the normal incidence beam from reaching detectors 88 and 90.

The detection subsystem also includes ellipsoidal mirror 92, beam splitter 94, and detectors 96 and 98, which form a "wide channel" of the detection subsystem. In other words, light scattered from the illuminated area on the wafer along directions relatively far from normal to the surface of the wafer is collected and focused by ellipsoidal mirror 92. In this manner, ellipsoidal mirror 92 collects light scattered from the wafer at relatively "wide" scattering angles. The light from the wafer that is collected by ellipsoidal mirror 92 may include diffusely scattered light. Ellipsoidal mirror 92 directs the collected light to beam splitter 94. Beam splitter 94 is configured to direct one portion of the light to detector 96 and the other portion of the light to detector 98. One detector may be used to detect light scattered at relatively wide angles due to illumination by the normal incidence beam, and the other detector may be used to detect light scattered at relatively wide angles due to illumination by the oblique incidence beam. Detectors 96 and 98 may include any suitable detectors known in the art (e.g., PMTs). In addition, detectors 96 and 98 may be similarly or differently configured. The wide channel portion of the detection subsystem may include any other optical components (not shown) known in the art. For example, one or more spectral filtering components (e.g., bandpass filters) may be placed in the path of the collected light between beam splitter 94 and each of detectors 96 and 98.

Detectors 88, 90, 96, and 98 are configured to generate output responsive to the light scattered from the wafer. Processor 100 is coupled to detectors 88, 90, 96, and 98 by transmission media as shown by the dotted lines in FIG. 7. The transmission media may include any suitable transmission media known in the art. In addition, one or more additional components (not shown) may be interposed between each of the detectors and the processor such as analog-to-digital converters. In this manner, output generated by the detectors can be sent to and received by the processor. The processor is configured to determine a characteristic of the wafer using the output as described further herein.

As described above, the inspection subsystem includes multiple channels (e.g., the wide channel and the normal channel). In this manner, the inspection subsystem may be configured to generate the output using the multiple channels. The multiple channels are configured to detect light with different parameters (e.g., different wavelengths, different angles of incidence, different angles of collection, or some combination thereof). The output of one of the channels may be sensitive to one characteristic of the wafer (e.g., roughness), and another of the channels may be sensitive to another characteristic of the wafer (e.g., thickness). In this manner, the output produced by the different channels of the inspection subsystem may be used independently or separately to determine different characteristics of the wafer. For example, processor 100 may be configured to determine one characteristic of the wafer using the second output generated by one of the multiple channels and to determine another characteristic of the wafer using the second output generated by another of the multiple channels. Processor 100 may be further configured as described herein. The system shown in FIG. 7 may be further configured as described herein. In addition, the system shown in FIG. 7 has all of the advantages of the methods described above.

The system shown in FIG. 7 may also include carrier medium 102. Program instructions 104 for implementing methods such as those described herein may be transmitted over or stored on the carrier medium. In particular, carrier medium 102 includes program instructions 104 executable on processor 100 for performing one or more steps of the methods described herein. For example, in one embodiment, carrier medium 102 includes program instructions 104 executable on a computer system such as processor 100 for performing a method for determining a characteristic of wafer 70. The carrier medium and the program instructions may be further configured as described herein.

In some embodiments, the systems described herein may be configured as "stand alone tools" or tools that are not physically coupled to a process tool. However, such a system may be coupled to the process tool (not shown) by a transmission medium, which may include wired and wireless portions. The process tool may include any process tool known in the art such as a lithography tool, an etch tool, a deposition tool, a polishing tool, a plating tool, a cleaning tool, or an ion implantation tool. The process tool may be configured as a cluster tool or a number of process modules coupled by a common handler.

The results of the inspection performed by the methods and systems described herein may be used to alter a parameter of a process or a process tool using a feedback control technique, a feedforward control technique, and/or an in situ control technique. The parameter of the process or the process tool may be altered manually or automatically.

The embodiments described herein may include any step(s) of any method(s) described in commonly assigned U.S. patent application Ser. Nos. 11/561,659 by Zafar et al. and 11/561,735 by Kulkarni et al., both of which were filed on Nov. 20, 2006, and both of which are incorporated by reference as if fully set forth herein. In addition, the embodiments of the system described herein may be further configured as described in these patent applications.

Further modifications and alternative embodiments of various aspects of the invention may be apparent to those skilled in the art in view of this description. For example, methods and systems for determining a characteristic of a wafer are provided. Accordingly, this description is to be construed as illustrative only and is for the purpose of teaching those skilled in the art the general manner of carrying out the invention. It is to be understood that the forms of the invention shown and described herein are to be taken as the presently preferred embodiments. Elements and materials may be substituted for those illustrated and described herein, parts and processes may be reversed, and certain features of the invention may be utilized independently, all as would be apparent to one skilled in the art after having the benefit of this description of the invention. Changes may be made in the elements described herein without departing from the spirit and scope of the invention as described in the following claims.

What is claimed is:

1. A method for determining roughness of a wafer, comprising:

generating output responsive to light from the wafer using an inspection system, wherein the output comprises first output corresponding to defects on the wafer and second output that does not correspond to the defects, and wherein the first and second output are generated by the same detector; and determining a value for the roughness of the wafer using the second output and not the first output, wherein said determining comprises determining the value for the roughness using a predetermined correlation between the second output and the roughness, wherein the roughness is a non-defect related characteristic of the wafer that can be measured using a metrology tool, and wherein the roughness is a physical quantity of the wafer.

2. A method for determining reflectivity of a film formed on a wafer, comprising:

generating output responsive to light from the wafer using an inspection system, wherein the output comprises first output corresponding to defects on the wafer and second output that does not correspond to the defects, and wherein the first and second output are generated by the same detector; and determining a value for the reflectivity of the film formed on the wafer using the second output and not the first output, wherein said determining comprises determining the value for the reflectivity of the film using a predetermined correlation between the second output and the reflectivity of the film, wherein the reflectivity of the film is a non-defect related characteristic of the wafer that can be measured using a metrology tool.

3. A method for determining a thickness of a film formed on a wafer; comprising:
generating output responsive to light from the wafer using an inspection system, wherein the output comprises first output corresponding to defects on the wafer and second output that does not correspond to the defects, and wherein the first and second output are generated by the same detector; and
determining a value for the thickness of the film formed on the wafer using the second output and not the first output, wherein said determining comprises determining the value for the thickness of the film using a predetermined correlation between the second output and the thickness of the film, wherein the thickness of the film is a non-defect related characteristic of the wafer that can be measured using a metrology tool, and wherein the thickness of the film is a physical quantity of the wafer.

4. A method for determining a polish uniformity of a film formed on a wafer, comprising:
generating output responsive to light from the wafer using an inspection system, wherein the output comprises first output corresponding to defects on the wafer and second output that does not correspond to the defects, and wherein the first and second output are generated by the same detector; and
determining a value for the polish uniformity of the film formed on the water using the second output and not the first output, wherein said determining comprises determining the value for the polish uniformity of the film using a predetermined correlation between the second output and the polish uniformity of the film, wherein the polish uniformity of the film is a non-defect related characteristic of the wafer that can be measured using a metrology tool, and wherein the polish uniformity of the film is a physical quantity of the wafer.

5. A method for determining a resistivity of a film formed on a wafer, comprising:
generating output responsive to light from the wafer using an inspection system, wherein the output comprises first output corresponding to defects on the wafer and second output that does not correspond to the defects, and wherein the first and second output are generated by the same detector; and
determining a value for the resistivity of the film formed on the water using the second output and not the first output, wherein said determining comprises determining the value for the resistivity of the film using a predetermined correlation between the second output and the resistivity of the film, wherein the resistivity of the film is a non-defect related characteristic of the wafer that can be measured using a metrology tool, and wherein the resistivity of the film is a physical quantity of the wafer.

6. A method for determining a grain size of a film formed on a wafer, comprising:
generating output responsive to light from the wafer using an inspection system, wherein the output comprises first output corresponding to defects on the wafer and second. output that does not correspond to the defects, and wherein the first and second output are generated by the same detector; and
determining a value for the grain size of the film formed on the wafer using the second output and not the first output, wherein said determining comprises determining the value for the grain size of the film using a predetermined correlation between the second output and the grain size of the film, wherein the grain size of the film is a non-defect related characteristic of the wafer that can be measured using a metrology tool, and wherein the grain size of the film is a physical quantity of the wafer.

7. The method of claim 1, wherein the light from the wafer comprises diffusely scattered light.

8. The method of claim 1, further comprising performing inline monitoring of a semiconductor fabrication process using the roughness to detect excursions in the semiconductor fabrication process.

9. The method of claim 1, further comprising determining variation in the second output across the wafer and determining if the variation is associated with a signature of a process tool used to form the wafer.

10. The method of claim 1, further comprising generating a two-dimensional map of the second output across substantially an entire surface of the wafer, determining if an abnormal pattern is present in the two-dimensional map, and if an abnormal pattern is present, determining if the abnormal pattern corresponds to an excursion in a process used to form the wafer.

11. The method of claim 1, wherein the output further comprises haze measurements.

12. The method of claim 2, wherein the light from the wafer comprises diffusely scattered light.

13. The method of claim 2, further comprising performing inline monitoring of a semiconductor fabrication process using the reflectivity to detect excursions in the semiconductor fabrication process.

14. The method of claim 2, further comprising determining variation in the second output across the wafer and determining if the variation is associated with a signature of a process tool used to form the wafer.

15. The method of claim 2, further comprising generating a two-dimensional map of the second output across substantially an entire surface of the wafer, determining if an abnormal pattern is present in the two-dimensional map, and if an abnormal pattern is present, determining if the abnormal pattern corresponds to an excursion in a process used to form the wafer.

16. The method of claim 2, wherein the output further comprises haze measurements.

17. The method of claim 3, wherein the light from the wafer comprises diffusely scattered light.

18. The method of claim 3, further comprising performing inline monitoring of a semiconductor fabrication process using the thickness to detect excursions in the semiconductor fabrication process.

19. The method of claim 3, further comprising determining variation in the second output across the wafer and determining if the variation is associated with a signature of a process tool used to form the wafer.

20. The method of claim 3, further comprising generating a two-dimensional map of the second output across substantially an entire surface of the wafer, determining if an abnormal pattern is present in the two-dimensional map, and if an abnormal pattern is present, determining if the abnormal pattern corresponds to an excursion in a process used to form the wafer.

21. The method of claim 3, wherein the output further comprises haze measurements.

22. The method of claim 4, wherein the light from the wafer comprises diffusely scattered light.

23. The method of claim 4, further comprising performing inline monitoring of a semiconductor fabrication process using the polish uniformity to detect excursions in the semiconductor fabrication process.

24. The method of claim 4, further comprising determining variation in the second output across the wafer and determining if the variation is associated with a signature of a process tool used to form the wafer.

25. The method of claim 4, further comprising generating a two-dimensional map of the second output across substantially an entire surface of the wafer, determining if an abnormal pattern is present in the two-dimensional map, and if an abnormal pattern is present, determining if the abnormal pattern corresponds to an excursion in a process used to form the wafer.

26. The method of claim 4, wherein the output further comprises haze measurements.

27. The method of claim 5, wherein the light from the wafer comprises diffusely scattered light.

28. The method of claim 5, further comprising performing inline monitoring of a semiconductor fabrication process using the resistivity to detect excursions in the semiconductor fabrication process.

29. The method of claim 5, further comprising determining variation in the second output across the wafer and determining if the variation is associated with a signature of a process tool used to form the wafer.

30. The method of claim 5, further comprising generating a two-dimensional map of the second output across substantially an entire surface of the wafer, determining if an abnormal pattern is present in the two-dimensional map, and if an abnormal pattern is present, determining if the abnormal pattern corresponds to an excursion in a process used to form the wafer.

31. The method of claim 5, wherein the output further comprises haze measurements.

32. The method of claim 6, wherein the light from the wafer comprises diffusely scattered light.

33. The method of claim 6, further comprising performing inline monitoring of a semiconductor fabrication process using the grain size to detect excursions in the semiconductor fabrication process.

34. The method of claim 6, further comprising determining variation in the second output across the wafer and determining if the variation is associated with a signature of a process tool used to form the wafer.

35. The method of claim 6, further comprising generating a two-dimensional map of the second output across substantially an entire surface of the wafer, determining if an abnormal pattern is present in the two-dimensional map, and if an abnormal pattern is present, determining if the abnormal pattern corresponds to an excursion in a process used to form the water.

36. The method of claim 6, wherein the output further comprises haze measurements.

* * * * *